United States Patent [19]

Hughes

[11] Patent Number: 4,463,096
[45] Date of Patent: Jul. 31, 1984

[54] PETROLEUM SOURCE ROCK IDENTIFICATION

[75] Inventor: William B. Hughes, Osage County, Okla.

[73] Assignee: Phillips Petroleum Company, Bartlesville, Okla.

[21] Appl. No.: 321,507

[22] Filed: Nov. 16, 1981

[51] Int. Cl.³ .................... G01N 21/72; G01N 31/08
[52] U.S. Cl. ...................................... 436/29; 73/23.1; 436/91; 436/120; 436/140; 436/161; 436/171
[58] Field of Search .............................. 436/29-31, 436/91, 120, 171, 140, 161; 73/23.1

[56] References Cited

U.S. PATENT DOCUMENTS 4,111,554  9/1978  Colin et al. ................... 73/23.1

OTHER PUBLICATIONS

Sulfur Compounds in Petroleum, Thompson et al., ASTM Symposium, Jan. 1965.
Johansen, Use of a Flame Photometric Detector with Glass Open Tubular Columns, for the Analysis of Sulfur Compounds in Petroleum Products, Chromatography Newsletter, vol. 5, No. 3, Sep. 1977.
Coleman et al., Identification of Benzo(b)thiophene and its 2- and 3-Methyl Homologs in Wasson, Texas, Crude Oil, J. Chem. Engr. Data 6, 464-8, (1961).
Ho et al., Evolution of Sulfur Compounds in Crude Oils, 44 page Bull. 58, 2338-2348, (1974).
Abstracts of Papers, ACS Meeting (1979), The Origin of Sour Petroleums, William Hughes.
Abstract, Geological Society of America Meeting, May 1980, Carbonates and the Petroleum Geochemistry of Sulfur, William Hughes.

Primary Examiner—Michael S. Marcus

[57] ABSTRACT

The geochemical oil prospecting method is disclosed in which a crude oil sample is analyzed for the presence of distinctive patterns of aromatic sulfur compounds which are indicative of the petroleum source rock type. Using relative proportions of benzothiophenes, dibenzothiophene, isomeric methyl dibenzothiophenes, dimethyl- and trimethydibenzothiophenes a crude oil can be identified as having a carbonate or siliciclastic source. The information obtained can be used in combination with geological and seismic studies to determine potential oil locations.

16 Claims, 13 Drawing Figures

FIG. 13

PETROLEUM SOURCE ROCK IDENTIFICATION

BACKGROUND OF THE INVENTION

This invention relates to methods of geochemical prospecting for petroleum. In one aspect, it relates to the determination of petroleum source rock type. In another aspect, the invention relates to analysis of a sample of crude oil to determine its source rock type from the relative amounts of certain organosulfur compounds present in the crude oil.

Modern methods of oil exploration involve the use of a combination of seismic and geochemical prospecting methods. Geochemical prospecting methods have developed from an understanding of the ways in which petroleum originated and migrated to a particular location. It is known that petroleum has an organic origin and has developed from the remains of living organisms which were deposited into sediments. The sediments were then buried and the action of temperature over time converted the organic matter to petroleum. It is believed that petroleum found in reservoirs today has often migrated to those reservoirs from the original location of petroleum generation.

In exploring for oil, it is useful to know the locations of such oil-generating formations, which can then be used in combination with seismic and geological data from the region to predict the locations of other oil-bearing reservoirs to which oil may have migrated from such common source formations. If information on the type of source rock could be obtained from a petroleum sample, this information could be used in finding the source formation and in targeting future drilling at this formation and proximal traps.

It is therefore an object of the invention to provide a method of geochemical oil exploration. It is a further object to provide a method of determining from a chemical analysis of an oil sample the type of source rock in which it was generated.

SUMMARY OF THE INVENTION

According to the invention, the organic sulfur components of a sample of petroleum are analyzed in order to determine the source rock type of the petroleum. The thiophenic sulfur content of the petroleum is determined and the results are analyzed for the presence of certain patterns. The method can involve the use of a gas chromatograph equipped with a sulfur-sensitive detector to determine the relative amounts of benzothiophenes, dibenzothiophene, methyldibenzothiophenes, dimethyldibenzothiophenes, and trimethyldibenzothiophenes in an oil sample. Significant amounts of benzothiophenes relative to dibenzothiophenes are an indication of a carbonate source rock. A further indication of a carbonate source is a pattern in the relative amounts of three isomeric methyl dibenzothiophenes such that the quantities of the first and last major isomers (A- and C-isomers) to elute are each greater than the quantity of the second major isomer (B-isomer) to elute. A comparable abundance of methyl-, dimethyl- and trimethyl-dibenzothiophenes is a further indication of carbonate source rock. In contrast, petroleum from siliciclastic source rocks is characterized by little or no benzothiophenes content; a quantity of methyldibenzothiophene A-isomer which is great in comparison with the amount of B-isomer, which in turn is larger than or equal to the amount of C isomer; and a quantity of dibenzothiophene and methyldibenzothiophenes which is great in comparison with dimethyl- and trimethyldibenzothiophenes.

The invention oil prospecting method involves the chemical analysis of petroleum to determine the relative amounts of benzothiophenes, dibenzothiophene, isomeric methyldibenzothiophenes, dimethyldibenzothiophenes, and trimethyldibenzothiophenes, and the subsequent identification based on the analysis results of the petroleum source rock type. The identification can be used, in combination with seismic and other petroleum exploration methods, to select oil drilling sites.

DETAILED DESCRIPTION OF THE INVENTION

The invention method aids in petroleum exploration by distinguishing between petroleum from a carbonate source rock and petroleum from a siliciclastic source rock. The invention is based on the discovery that oil from carbonate source rocks contains certain distinctive patterns of organosulfur constituents. Aromatic sulfur compounds appear to be good "fingerprint" constituents of crude oil because they are less susceptible to biodegradation than some other constituents of oil.

As known in the art, the term "carbonate" refers to a sedimentary rock which contains at least about 50 percent by weight the carbonates of calcium and/or magnesium. "Siliciclastic" refers to a fine-grained (less than 100μ average particle size) sedimentary rock consisting principally of silicate minerals.

The substance analyzed in the invention method is a sample of surface or subsurface crude oil. Pre-analysis treatment of the sample can vary with the type of sample and the analytical procedure to be applied. For gas chromatographic analysis, a crude oil will generally be separated into three fractions—saturates, aromatics and asphaltics—by liquid chromtography on silica gel, and the aromatics fraction then used, generally in the form of a hydrocarbon solution, for the analysis.

Chemical analysis of the oil or oil fraction can be performed by high-resolution gas chromatography (GC) coupled with a sulfur-sensitive detector such as a flame photometric detector (FPD). Such a method enables rapid determination of the organosulfur composition of crude oils. A suitable analysis method is as follows: An n-hexane solution of the aromatic fraction is injected into a suitable GC column at an injection temperature of 150°–500° C., preferably about 300° C. The column temperature is programmed for an initial temperature of 50°–100° C., generally about 80° C., heating at 5°–50° C., preferably 15° C., per minute to 150°–300° C., preferably 200° C., with a 5 minute hold, followed by heating at 2°–20° C., generally 4° C. per minute with a 30 minute hold. A suitable GC analyzer is the Perkin Elmer Sigma ® 10 gas chromatograph equipped with a flame photometric detector.

The gas chromatograms or other data obtained are examined for patterns which distinguish carbonate source rocks from siliciclastic source rocks. Three classes of organosulfur compounds can typically be found in the aromatic fraction of crude oil; the benzothiophenes, dibenzotiophenes, and benzonaphthothiophenes. The benzothiophenes consist of three families: the 2-carbon, 3-carbon and 4- and higher-carbon substituted derivatives. The substituents are believed to be mainly methyl groups. The dibenzothiophenes consist primarily of dibenzothiophene itself and its methyl, dimethyl and trimethyl derivatives. A third family of compounds, benzonaphthothiophene and its $C_1$–$C_5$-substituted derivatives, is generally present in much smaller amounts than the benzo- and dibenzothiophenes. The various peaks distinguishable in the FPD trace within each thiophenic family correspond primarily to positional isomers. For example, there are fifteen possible isomers for dimethyldibenzothiophene.

Figure 1:
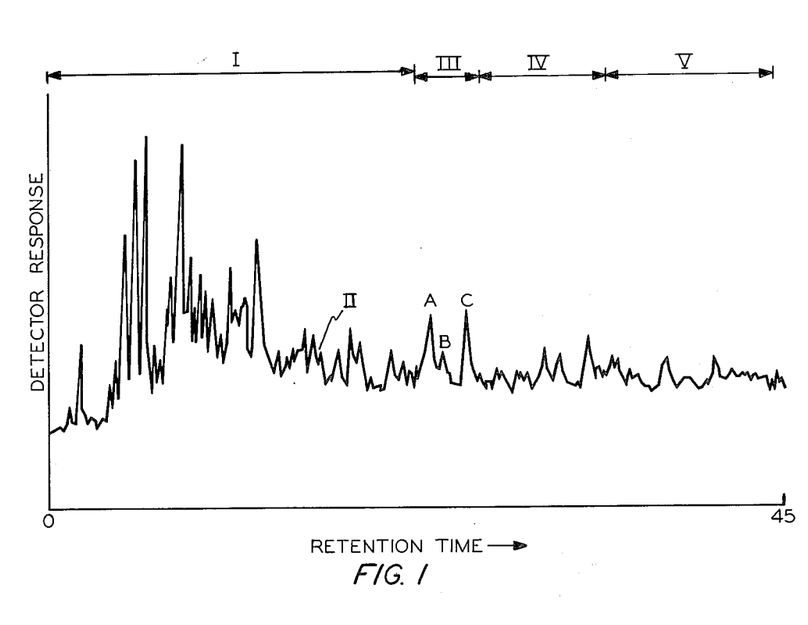
FIG. 1 is a gas chromatogram of a calibration sample of the aromatic fraction of petroleum from the Sunniland Formation, Felda Field (Florida) showing the characteristic pattern of petroleum from a carbonate source.
Figure 2:
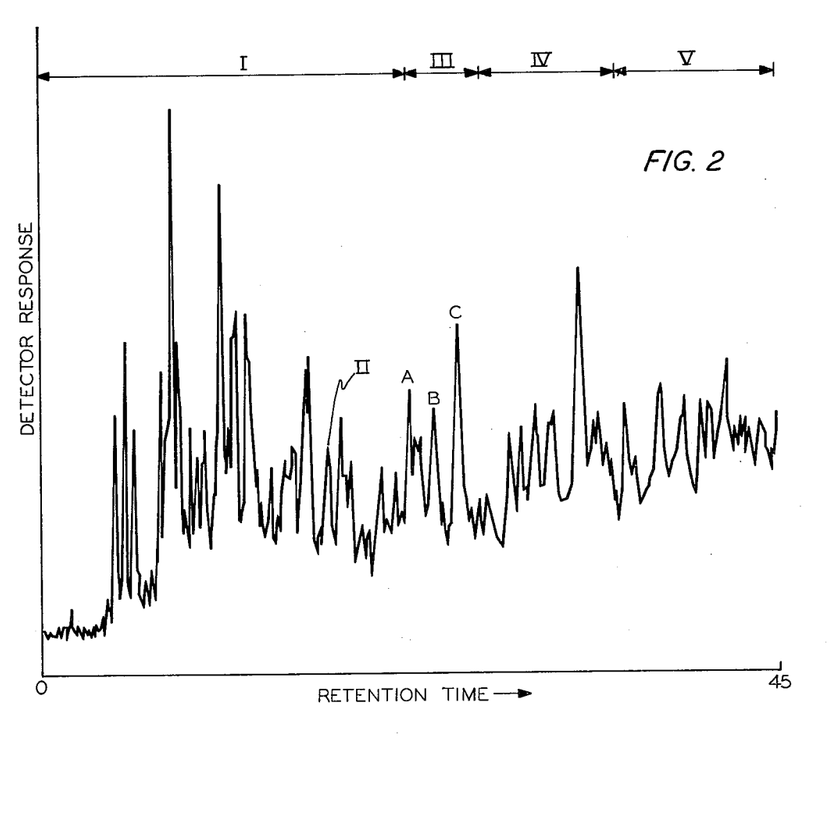
FIG. 2 is a gas chromatogram of a calibartion sample of the aromatic fraction of petroleum from the Smackover Formation, Toxey Field (Alabama) showing the characteristic pattern of petroleum from a carbonate source.

The patterns characteristic of crude oil from a carbonate source rock can be seen by reference to FIGS. 1 and 2, which are gas chromatograms of crude oil samples known to have carbonate sources. Carbonate oils are generally characterized by significant amounts of benzothiophenes, as indicated by rather large, distinct peaks which elute from the column early in the analysis. The quantity of benzothiophenes will generally be at least equal to the quantity of dibenzothiophenes. In FIGS. 1 and 2, the peaks in the region labelled I (excluding dibenzothiophene) represent significant quantities of benzothiophenes, while the dibenzothiophene peak (II) indicates a relatively insignificant quantity of dibenzothiophene. (Retention times listed ar approximate.)

Carbonate oils are further characterized by a rough V-pattern in the heights of the peaks of three isomeric methyldibenzothiophenes, so that A-isomer$\geq$C-isomer$>$B-isomer, A designating the peak which elutes first, B the next peak, and C the last of the three to elute from the column (under the column conditions specified in the Example). Although there are four possible isomers of methyldibenzothiophene, the invention method makes use of the three major isomers present in a typical carbonate or siliciclastic oil sample. The location of the peak for the fourth isomer has not at this time been determined, although it is believed to be represented by a relatively minor peak between A and B. The presence or absence of this fourth isomer does not materially alter the interpretation of the results of source rock analysis. Useful results are obtained by determining or examining the relative sizes of the three major peaks representing the three major isomeric methyldibenzothiophenes present. FIGS. 1 and 2 illustrate the characteristic methyldibenzthiophene pattern of a carbonate source, while FIGS. 3 and 4 exhibit the A-isomer$>$B-isomer$\geq$C-isomer pattern which is generally indicative of a non-carbonate oil, with the exception for mature carbonate crude oils discussed below.

Figure 3:
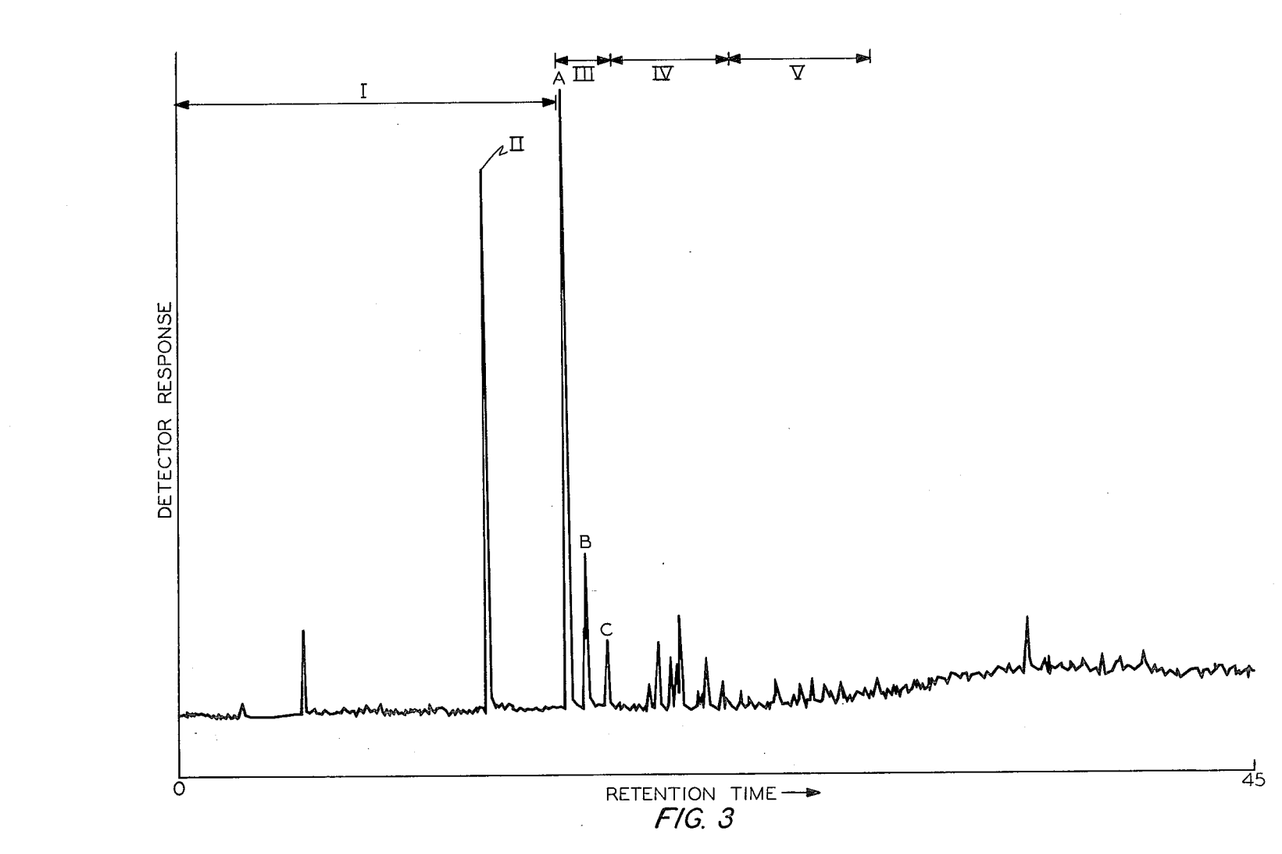
FIG. 3 is a gas chromatogram of a calibration sample of the aromatic fraction of petroleum from the Klasaman Formation, Salawiti Island (Indonesia) showing the characteristic pattern of petroleum from a siliciclastic source.
Figure 4:
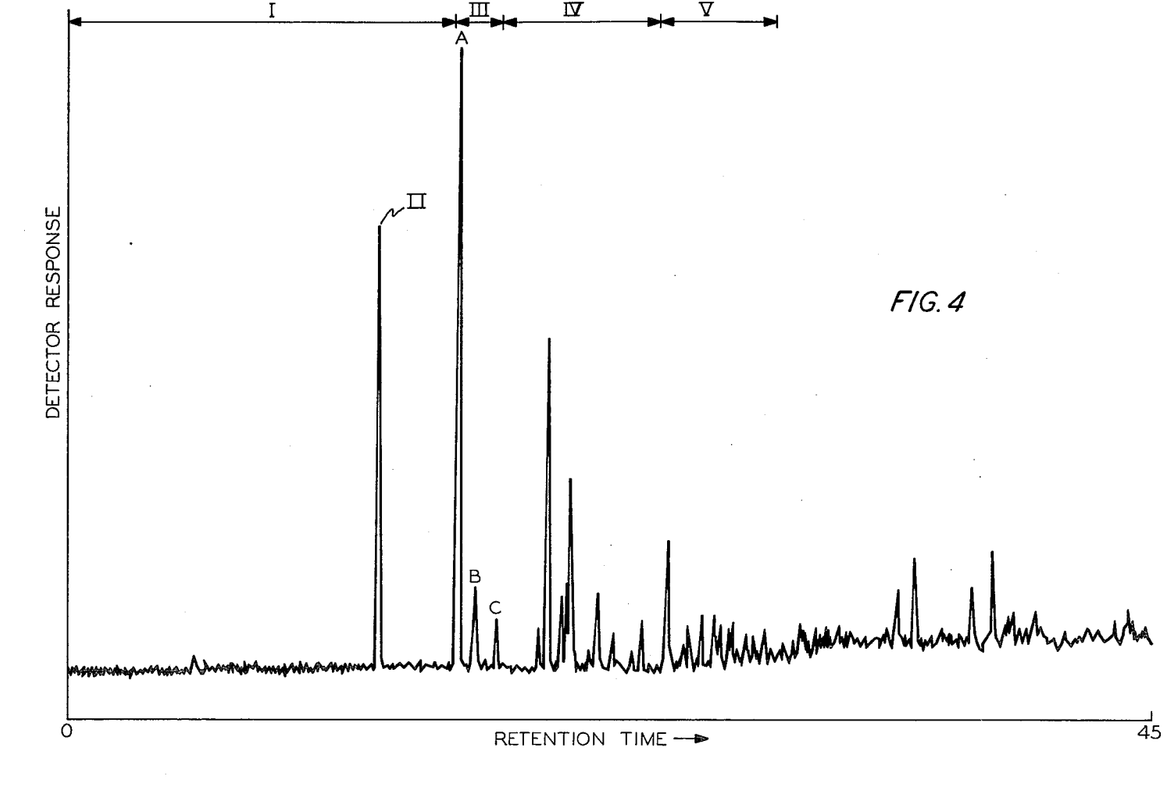
FIG. 4 is a gas chromatogram of a calibration sample of the aromatic fraction of petroleum from the McKee Formation, Andector Field (Texas) showing the characteristic pattern of petroleum from a siliciclastic source.

A crude oil from a carbonate source rock is further characterized by a comparable abundance of methyl-, dimethyl- and trimethyldibenzothiophenes, as shown in FIGS. 1 and 2 in the regions III, IV and V (III is approximately equal to IV is approximately equal to V). By contrast, the peaks in the corresponding areas of FIGS. 3 and 4 show dibenzothiophenes and methyldibenzothiophenes predominating over dimethyl- and trimethyldibenzothiophenes (combined areas II and III vs. combined areas IV and V). The relative amounts of methyl-, dimethyl-, and trimethyldibenzothiophenes in a carbonate oil are generally such that no one peak area will vary widely from that of another. Generally, in a carbonate oil, no one total peak area in any one of the designated regions III, IV and V will be more than twice that of any of the other two.

In summary, oils from carbonate sources in general possess distinctive organosulfur fingerprints characterized by an abundance of benzothiophenes, a fairly even distribution among the substituted dibenzothiophenes and a distinctive isomer distribution among the methyldibenzothiphenes. This pattern is modified by thermal maturation, resulting in the carbonate oil signature becoming less distincitve but still discernible.

Figure 13:
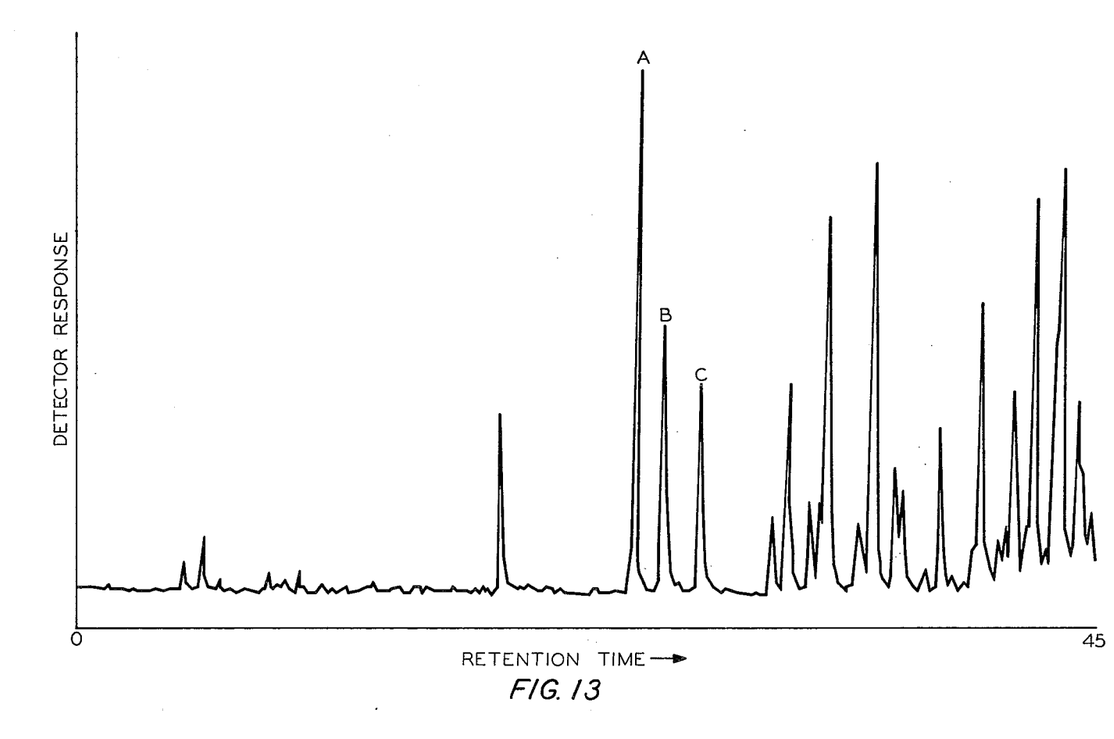
FIG. 13 is a gas chromatogram of the aromatic fraction of a mature crude oil sample which exhibits the characteristics of mature petroleum from a carbonate source.

Carbonate oils of a high degree of thermal maturity may show some modification of the pattern. In such crude oils, the benzothiophenes are not as abundant and the C-isomer of the methyldibenzothiophenes is less pronounced relative to the A- and B-isomers, resulting in a pattern of A-isomer$>$B-isomer$\geq$C-isomer. If a gas chromatogram of a mature carbonate oil exhibits the departures from the carbonate pattern discussed above, the carbonate source can nevertheless be identified by the relative abundance of methyl-, dimethyl- and trimethyldibenzothiophenes. In the carbonate oils, it will generally be observed that the distribution of the substituted dibenzothiophenes is relatively uniform, while the siliciclastic oils evidence of declining amount of dimethyl- and trimethyldibenzothiophenes relative to the methyldibenzothiophenes. A pattern characteristic of a mature carbonate crude oil is shown in FIG. 13. Maturity of a crude oil can be assessed by various means known in the art, such as API gravity, total sulfur content, and percent saturates.

By contrast, aromatic fractions of crude oil from a siliciclastic source rock are generally characterized by the absence of significant amounts of benzothiophenes. In FIGS. 3 and 4, for example, there are no significant peaks in the benzothiophene areas. Crude oil from siliciclastic source rock is further characterized by a C-isomer which is low in comparison with A- and B-isomer, producing a pattern of A-isomer > B-isomer ≧ C-isomer. Also characteristic of oil from a siliciclastic source is a combined quantity of dibenzothiophene and methyldibenzothiophenes (II and III) which predominates over dimethyl- and trimethyldibenzothiophenes (IV and V).

Identification of the characterizing organosulfur peaks on a gas chromatogram of an oil sample can be made by conventional means such as the use of an authentic sample to calibrate the GC instrument and determine the retention time of the components of interest. An alternative method of identifying the characterizing components is to use mass sepctrogrpahic detection of the eluting components to identify the compounds of interest.

A suitable microprocessor, for example the Perkin-Elmer Sigma 10, can be programmed to automatically calculate and compare the peak areas according to the criteria described above and to generate an output signal representative of the source rock type of the petroluem being analyzed.

EXAMPLES

Four samples of oil from different locations were evaluated according to the invention method to determine source rock type. The following procedure was used for each sample.

About 1 ml of each crude oil was diluted with 20-25 times its volume of n-hexane and stirred for about 20 minutes. The mixture was allowed to settle for 1 hour and was then filtered through a 0.3 micron Millipore ® filter. The filtrate was evaporated just to dryness at 40° C.

About 300 mg of the material recovered from the filtrate was diluted with about 1.5 ml n-hexane and subjected to liquid chromatography in a 90 mm×25 mm (o.d.) precolumn containing 63-200 μm particle size deactivated silica gel packing and a 310 mm×25 mm o.d. Lobar main column containing 40-63 μm LiChroprep Si-60 ® packing and n-hexane as the eluent pumped at the rate of 5 ml/min. The first fraction to elute is the saturate fraction, as evidenced by refractive index detector response. The second fraction, obtained by reversing the flow of eluent through the main column, is the aromatic fraction, as evidenced by ultraviolet absorption detector response. n-Hexane solvent was removed from the collected aromatics fraction on a rotary evaporator until a volume of 1-2 ml was reached. Evaporation was continued at 65°-70° C. just until dryness.

The recovered aromatics fraction was diluted with about 3 times its weight with n-hexane, the precise ratio of solvent to aromatic fraction being adjusted according to the concentration of thiophenic derivatives in the sample as determined from subsequent gas chromatography analysis. Approximately 1 μm of the mixture was used for GC analysis on a 60 m wall-coated open tubular glass capillary column. Typical analysis conditions were an injection temperature of 300° C. and the following column temperature program: 80° C. initial; heating at 15° C. per minute to 200° C. with a 5 minute hold; heating at 4° C. per minute to 280° C. with a 30 minute hold. The helium carrier gas flow rate was 1-2 ml per minute. GC analyses were done on a Perkin-Elmer Sigma ® 1B analyzer equipped with a flame-photometric detector. Peak areas were measured and normalized areas calculated and reduced to bar graphs by a Perkin Elmer Sigma 10 microprocessor.

Figure 5:
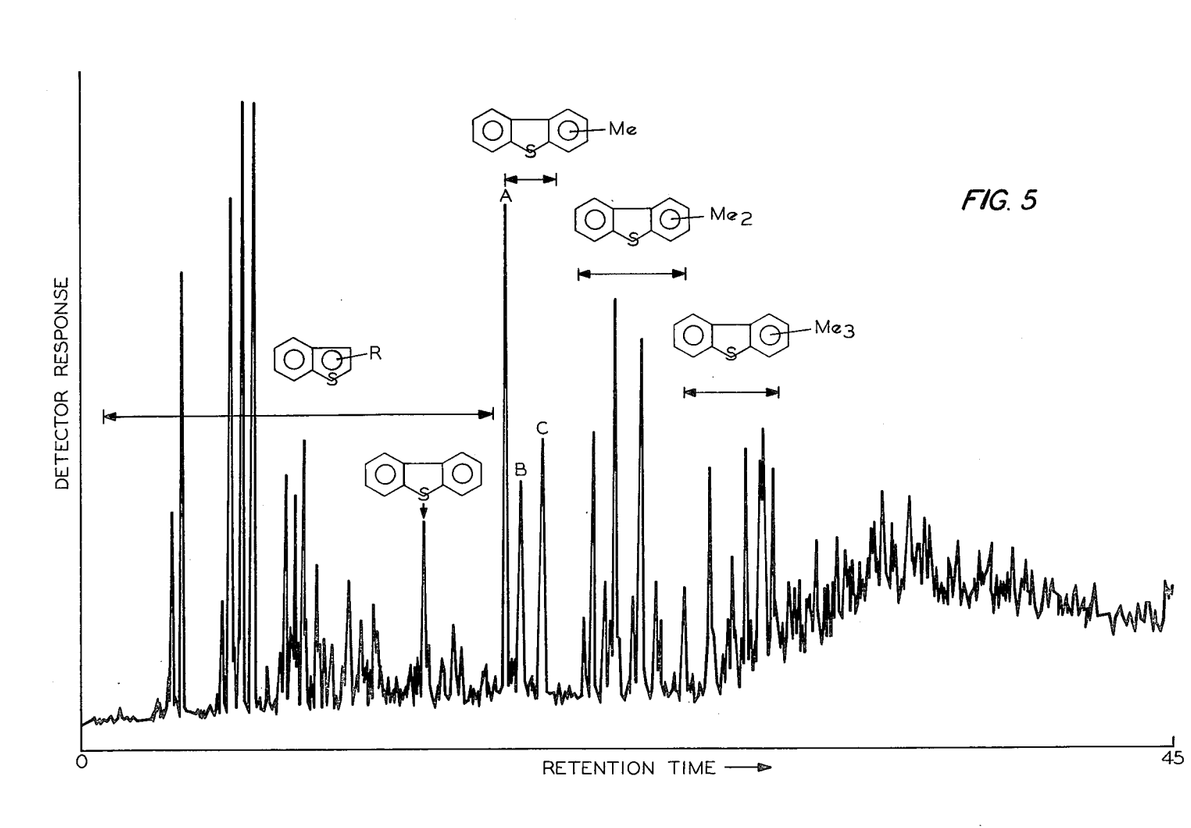
FIG. 5 is a gas chromatogram of the aromatic fraction of a crude oil sample which exhibits the characteristics of petroleum from a carbonate source rock.
Figures 6, 8:
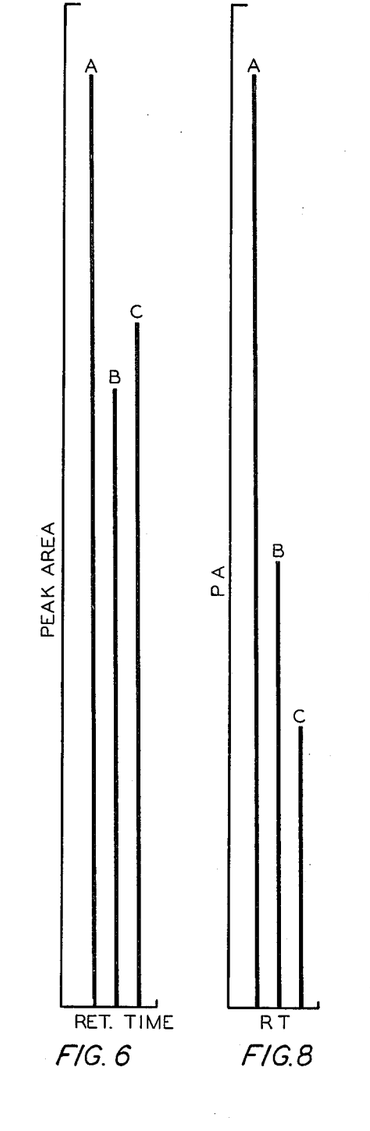
FIG. 6 is a graphic reproduction of a computer-generated comparison of the areas under the peaks labelled A, B, and C of the gas chromatogram of FIG. 5.
FIG. 8 is a graphic reproduction of a computer-generated comparison of the areas under the peaks labelled A, B, and C in the gas chromatogram of FIG. 7.

The gas chromatograms of FIGS. 5, 7, 9 and 11 were obtained from four crude oil samples from widely varying locations. The charts were examined for characteristic features indicating source rock type. FIG. 5 is readily identifiable as a gas chromatogram of a carbonate oil. The chormatogram shows the characteristic abundance of benzothiophenes, the V-pattern formed by the peaks of the three major isomeric methyldibenzothiophenes (peaks A, B and C) and the abundance of methyl-, dimethyl-, and trimethyldibenzothiophenes. FIG. 6 shows, in bar graph form, the normalized peak areas for the peaks labelled A, B and C.

Figure 7:
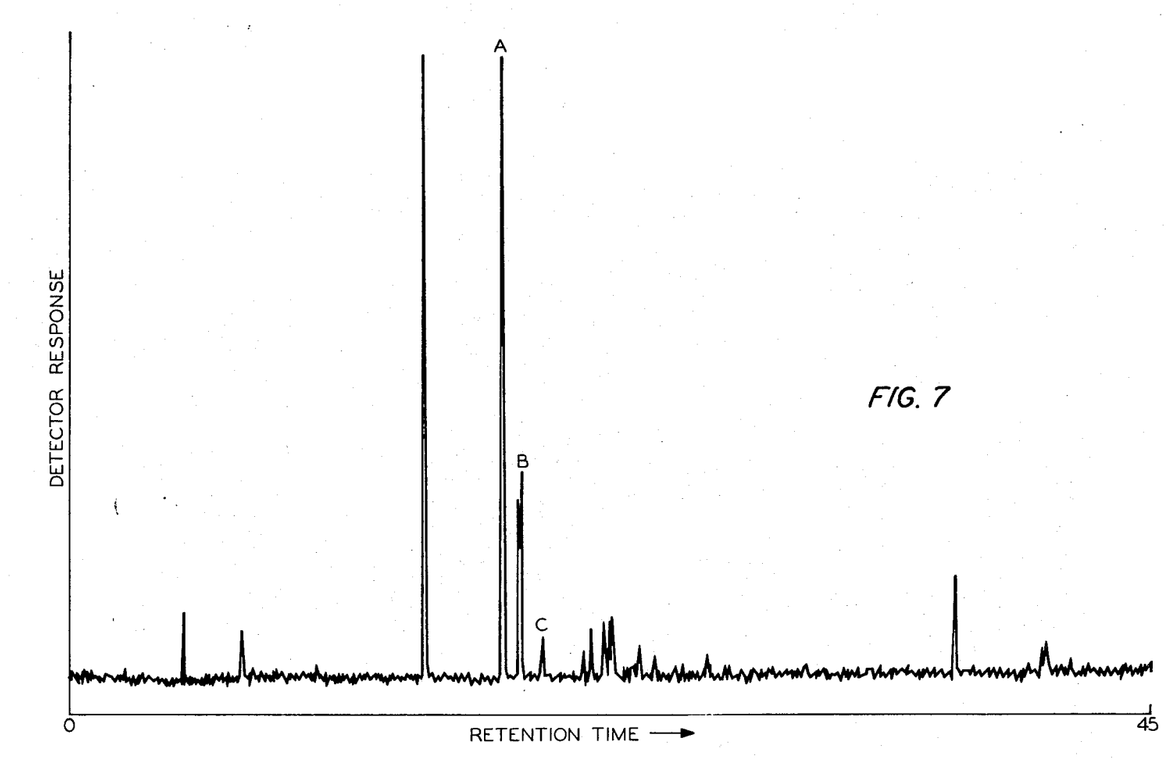
FIG. 7 is a graphic reproduction of a gas chromatogram of the aromatic fraction of a crude oil sample which exhibits the characteristics of petroleum from a siliciclastic source.

FIG. 7, by contrast, shows a gas chromatogram exhibiting the characteristic features of a siliciclastic oil. The chromatogram indicates a virtual absence of benzothiophenes, a stair-step pattern for the major isomeric methyldibenzothiophene peaks (A, B and C), and the relatively large amounts of dibenzothiophene and methyldibenzothiophenes compared with dimethyldibenzothiophenes and trimethyldibenzothiophenes. FIG. 8 shows, in bar graph form the normalized peak areas for the peaks labelled A, B and C.

Figure 9:
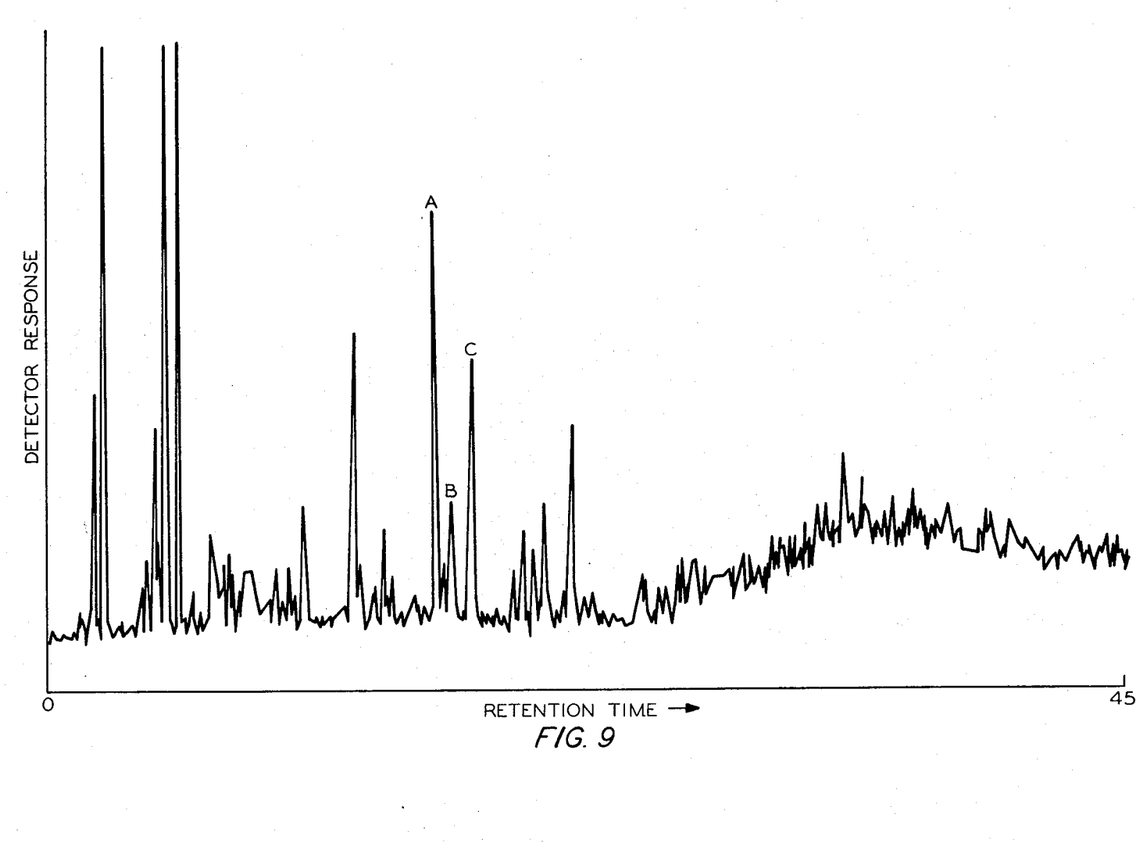
FIG. 9 is a gas chromatogram of the aromatic fraction of a crude oil sample which exhibits the characteristics of petroleum from a carbonate source.
Figures 10, 12:
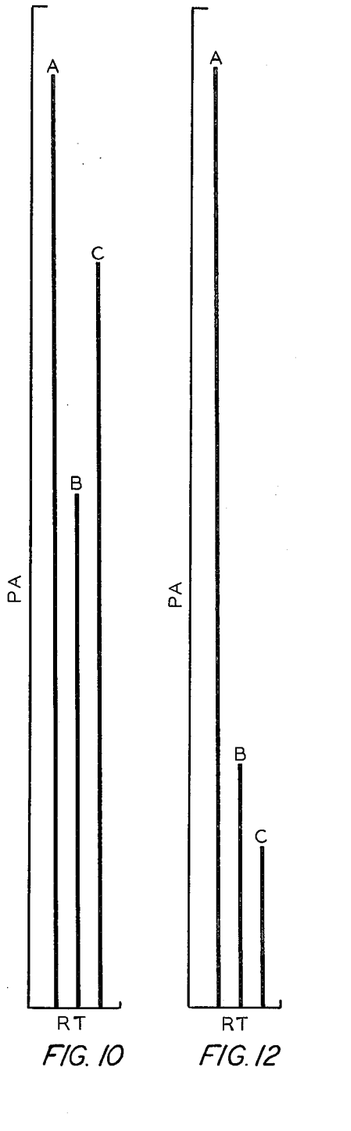
FIG. 10 is a graphic reproduction of a computer-generated comparison of the areas under the peaks labelled A, B, and C in the gas chromatogram of FIG. 9.
FIG. 12 is a graphic reproduction of a computer-generated comparison of the areas under the peaks labelled A, B, and C in the gas chromatogram of FIG. 10.
Figure 11:
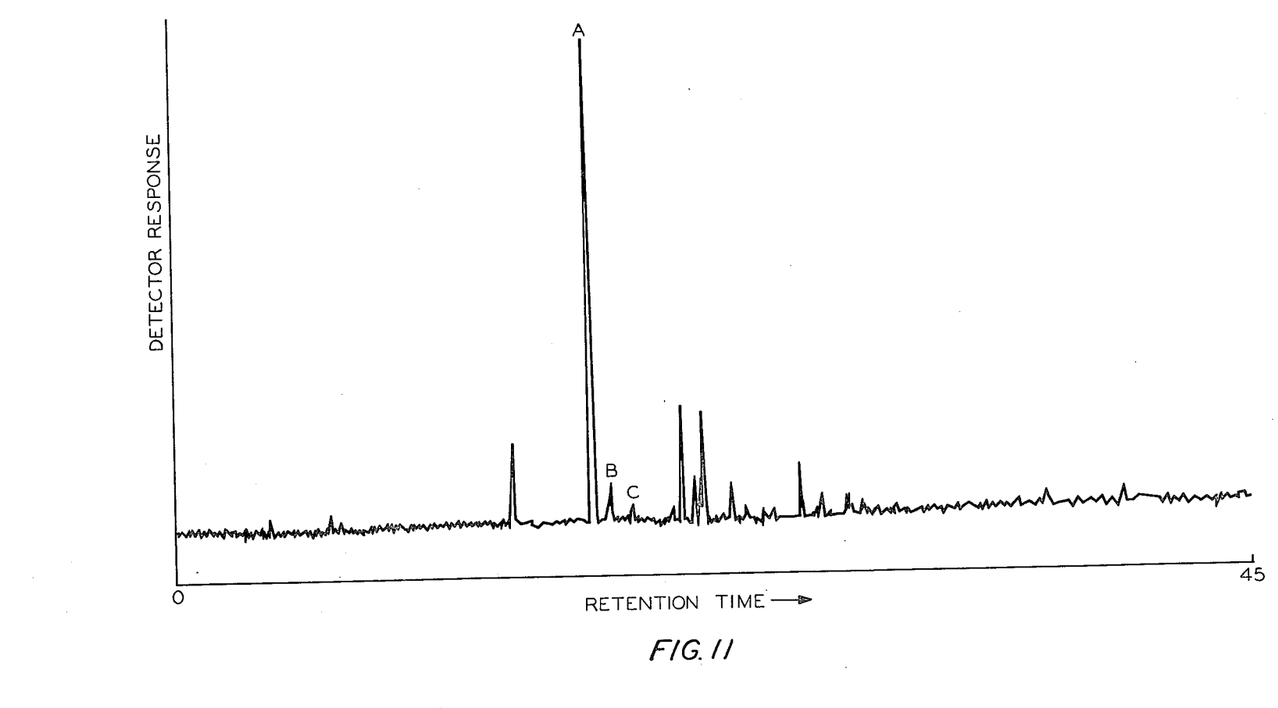
FIG. 11 is a gas chromatogram of the aromatic fraction of a crude oil sample which exhibits the characteristics of petroleum from a siliciclastic source.

Similarly, FIGS. 9 and 11 show gas chromatograms of the aromatic fractions of crude oils showing features characteristic of a carbonate oil and a siliciclastic oil, respectively. FIGS. 10 and 12 illustrate in bar graph form the areas under the isomeric peaks having the characteristic patterns.

I claim:
1. A method for determining the source rock type of a crude oil sample comprising:
   (a) determining the relative amounts of benzothiophenes and dibenzothiophenes in the sample of crude oil;
   (b) determining the relative amounts of the isomeric methyldibenzothiophenes present in the sample of crude oil;
   (c) determining the relative amounts of dimethyl- and trimethyldibenzothiophenes present in the sample of crude oil; and
   (d) identifying, on the basis of the results of steps a, b, and c, the source rock type of the crude oil sample.
2. The method of claim 1 which comprises performing steps a, b and c by gas chromatography using a chromatographic column.
3. The method of claim 2 which further comprises fractionating the crude oil into components including an aromatic fraction and performing steps a, b, and c and d with the aromatic fraction.
4. The method of claim 3 which comprises
   detecting the benzothiophenes and dibenzothiophenes which elute from the chromatographic column with a flame photometric detector and producing respective first and second sets of output signals representative of the amount of benzothiophenes and dibenzothiophenes detected, detecting first, second and third major isomers of methyldibenzothiophene which elute from the chromatographic column with a flame photometric detector and producing third, fourth and fifth output signals representative of the respective amounts detected, and detecting the dimethyl- and trimethyldibenzothiophenes which elute from the chromatographic column with a flame photometric detector and producing respective sixth and seventh sets of output signals proportional to the amount of dimethyl- and trimethyldibenzothiophenes detected.

5. The method of claim 4 which further comprises comparing the third, fourth and fifth output signals.

6. The method of claim 5 additionally comprising comparing the third, fourth and fifth signals and determining that the crude oil sample is from a carbonate source rock in response to the third signal being representative of an amount of first isomer at least equal to the amount of third isomer represented by the fifth signal and the fifth signal being representative of an amount of third isomer greater than the amount of second isomer represented by the fourth signal.

7. The method of claim 4 which further comprises comparing the first and second sets of output signals, comparing the third, fourth and fifth output signals, and comparing the combined second, third, fourth and fifth output signals with the combined sixth and seventh output signals.

8. The method of claim 7 additionally comprising determining that the crude oil sample is from a siliciclastic type source rock in response to the amount of first isomer represented by the third signal being at least equal to the amount of second isomer represented by the fourth signal, the amount of second isomer represented by the fourth signal being greater than the amount of third isomer represented by the fifth signal, and the combined amount of dibenzothiophene and methyldibenzothiophenes represented by the second set of output signals and the third, fourth and fifth output signals being greater than the combined amount of dimethyl- and trimethyldibenzothiophenes represented by the combined sixth and seventh sets of output signals.

9. The method of claim 7 which further comprises drilling a borehole proximate to a formation which corresponds in type to the identity of the source rock determined.

10. A method of geochemical oil prospecting which involves identifying a crude oil sample as having a carbonate source, the method comprising:
(a) extracting an organosulfur-containing aromatic fraction from the crude oil;
(b) injecting the aromatic fraction into a gas chromatograph column and separating on the column constituents comprising benzothiophenes, dibenzothiophenes, three major isomers of methyldibenzothiophenes, dimethyldibenzothiophenes and trimethyldibenzothiophenes;
(c) detecting each constituent as it elutes from the column and producing an output signal for each which is proportional to the amount of each constituent present;
(d) obtaining an output signal for benzothiophenes which is at least approximately equal to the output signal for dibenzothiophenes;
(e) obtaining an output signal for the first major isomer which is greater than or equal to the output signal for the third major isomer of methyldibenzothiophene which in turn is greater than the output signal for the second major isomer of methyldibenzothiophene the first, second and third major isomer being numbered in terms of their order of elution from the column; and
(f) obtaining output signals for methyl-, dimethyl- and trimethyldibenzothiophenes, none of which is more than twice the magnitude of any other of the three.

11. The method of claim 10 in which the constituents are detected by means of a flame photometric detector, the output signals are recorded as peaks on a gas chromatogram, and the areas under the peaks are automatically calculated.

12. The method of claim 10 in which the oil came from an underground reservoir and which further comprises performing a geologic and seismic study to locate oil reservoirs having carbonate source.

13. A method of geochemical oil prospecting which involves identifying a crude oil sample as having a siliciclastic source, the method comprising:
(a) extracting an organosulfur-containing aromatic fraction from the crude oil;
(b) injecting the aromatic fraction into a gas chromatograph column and separating on the column constituents comprising benzothiophenes, dibenzothiophenes, three major isomers of methyldibenzothiophene, dimethyldibenzothiophenes and trimethyldibenzothiophenes;
(c) detecting each constituent as it elutes from the column and producing an output signal for each which is representative of the amount of each constituent present;
(d) obtaining an output signal for benzothiophenes which is small in comparison with the output signal for dibenzothiophenes;
(e) obtaining an output signal for the first isomer of methyldibenzothiophene which is greater than or equal to the output signal for the second isomer, which in turn is greater than the output signal for the third isomer, the first, second and third isomers being numbered according to their order of elution from the column;
(f) obtaining combined output signals for dibenzothiophenes and methyldibenzothiophenes which are greater than the combined output signals for dimethyl- and trimethyldibenzothiophenes.

14. The method of claim 13 in which the constituents are detected by means of a flame photometric detector, the output signals are recorded as peaks on a gas chromatogram, and the areas under the peaks are automatically calculated.

15. The method of claim 13 in which the crude oil was obtained from an underground reservoir and which further comprises performing a seismic study to locate other oil reservoirs having a siliciclastic source.

16. A method of geochemical oil prospecting which involves identifying a mature crude oil sample as having a carbonate source, the method comprising:
(a) extracting an aromatic fraction from the crude oil;
(b) injecting the aromatic fraction into a gas chromatograph column and separating on the column constituents comprising benzothiophenes, dibenzothiophenes, three major isomers of methyldibenzothiophene, dimethyldibenzothiophenes and trimethyldibenzothiophenes;

(c) detecting each constituent as it elutes from the column and producing an output signal for each which is proportional to the amount of each constituent present;
(d) obtaining an output signal for benzothiophenes which is no greater than the output signal for dibenzothiophenes;
(e) obtaining an output signal for the first isomer of methyldibenzothiophene which is greater than the output signal for the second isomer which in turn is greater than or equal to the output signal for the third isomer, the first, second and third isomers being numbered according to their order of elution from the column; and
(f) obtaining combined output signals for dibenzothiophene and methyldibenzothiophenes which are no greater than the combined output signals for dimethylbenzothiophenes and trimethyldibenzothiophenes.

* * * * *